United States Patent
Kawamura (10) Patent No.: US 12,082,965 B2
(45) Date of Patent: Sep. 10, 2024

(54) POSITIONING DEVICE, POSITIONING METHOD, POSITIONING PROGRAM, RADIATION IMAGE PROCESSING DEVICE, RADIATION IMAGE PROCESSING METHOD, AND RADIATION IMAGE PROCESSING PROGRAM

(71) Applicant: FUJIFILM Corporation, Tokyo (JP)

(72) Inventor: Takahiro Kawamura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 17/707,570

(22) Filed: Mar. 29, 2022

(65) Prior Publication Data
US 2022/0313192 A1 Oct. 6, 2022

(30) Foreign Application Priority Data
Apr. 2, 2021 (JP) .................................. 2021-063572

(51) Int. Cl.
*A61B 6/04* (2006.01)
*A61B 6/00* (2006.01)
*A61B 6/50* (2024.01)

(52) U.S. Cl.
CPC .......... *A61B 6/5205* (2013.01); *A61B 6/0407* (2013.01); *A61B 6/505* (2013.01)

(58) Field of Classification Search
CPC .......... A61B 6/00; A61B 6/04; A61B 6/0407; A61B 6/0487; A61B 6/08; A61B 6/505; A61B 6/5205; A61B 6/5217; A61B 6/4452; A61B 6/5282
See application file for complete search history.

(56) References Cited

U.S. PATENT DOCUMENTS

| 10,448,913 B2 * | 10/2019 | Nakaya ................. A61B 6/488 |
| 2016/0140720 A1 | 5/2016 | Naito |
| 2018/0122094 A1 | 5/2018 | Naito |
| 2019/0362492 A1 | 11/2019 | Kawamura |

FOREIGN PATENT DOCUMENTS

| JP | 2002-126106 A | 5/2002 |
| JP | 2015-043959 A | 3/2015 |
| JP | 2019-202035 A | 11/2019 |
| WO | WO 2016/051603 | * 4/2016 |

* cited by examiner

*Primary Examiner* — Jurie Yun
(74) *Attorney, Agent, or Firm* — Studebaker & Brackett PC (57) ABSTRACT

A processor acquires a positioning image acquired by imaging a subject by a radiography apparatus, specifies a standard position in the positioning image and a reference position in a target structure included in the subject in the positioning image, and derives a relative movement amount of the top plate, the radiation source, and the radiation detector based on a deviation amount of the reference position from the standard position.

22 Claims, 8 Drawing Sheets

POSITIONING DEVICE, POSITIONING METHOD, POSITIONING PROGRAM, RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application claims priority under 35 U.S.C. § 119 to Japanese Patent Application No. 2021-063572 filed on Apr. 2, 2021. The above application is hereby expressly incorporated by reference, in its entirety, into the present application.

BACKGROUND

Technical Field

The present disclosure relates to a positioning device, a positioning method, a positioning program, a radiation image processing device, a radiation image processing method, and a radiation image processing program.

Related Art

In a bone system disease, such as osteoporosis, various methods for deriving a bone mineral density used for diagnosing a bone density have been proposed. For example, in JP2019-202035A, a method has been proposed in which a pixel value of a bone region of a subject is acquired from two radiation images obtained by irradiating the subject with two types of radiation having different energy distributions, and a bone mineral density in the bone region is derived for each pixel of the bone region based on an imaging condition, a body thickness of the subject, and the pixel value of the bone region.

On the other hand, in a case in which a radiation image of a subject lying on an imaging table is performed, the subject is positioned such that a target part is positioned at a desired position of the radiation image. As such a positioning method, a method has been proposed in which, from reference image data for specifying and diagnosing an affected part of a subject imaged in advance and positioning image data obtained by reading the inside of the subject as an image, a positioning error thereof is obtained, and the imaging table is horizontally moved based on the positioning error (see JP2002-126106A).

By the way, in a case in which the osteoporosis is diagnosed, it is important to perform the follow-up of increase/decrease in the bone mineral density. Therefore, in a case in which the bone mineral density is derived by using the radiation image, it is necessary to always perform reproducible imaging of the target bone under the same condition by positioning an optical axis of the radiation in an imaging apparatus to match the target bone in which the bone mineral density is to be derived.

However, the positioning of the subject depends on the skill of the radiological technician, and it may be difficult for some radiological technicians to position the target bone to match the optical axis of the radiation. In such a case, the radiological technician repeats trial and error at the time of imaging to allow the target bone to match the optical axis of the radiation. Therefore, the burden on the radiological technician who performs the positioning operation is heavy.

SUMMARY OF THE INVENTION

The present disclosure has been made in view of the above circumstances, and is to enable to easily perform reproducible positioning at the time of imaging of a subject.

The present disclosure relates to a positioning device of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the positioning device comprising at least one processor, in which the processor acquires a positioning image acquired by imaging the subject by the radiography apparatus, specifies a standard position in the positioning image and a reference position in a target structure included in the subject in the positioning image, and derives a relative movement amount of the top plate, the radiation source, and the radiation detector based on a deviation amount of the reference position from the standard position.

Note that, in the positioning device according to the present disclosure, the processor may specify the target structure in the positioning image, and may specify the reference position by deriving the reference position in the specified target structure.

In addition, in the positioning device according to the present disclosure, the processor may display the positioning image, and may specify the reference position by receiving designation of the reference position in the displayed positioning image.

In addition, in the positioning device according to the present disclosure, the processor may derive a magnification ratio of the target structure on the positioning image based on an imaging distance in a case in which the positioning image is acquired, and a distance between the radiation detector and the target structure, and derive the movement amount by correcting the deviation amount of the reference position from the standard position by the magnification ratio.

In addition, in the positioning device according to the present disclosure, the processor may derive a magnification ratio of the target structure on the positioning image based on an imaging distance in a case in which the positioning image is acquired, a body thickness of the subject, and a ratio of a position at which the target structure is present to the body thickness, and derive the movement amount by correcting the deviation amount of the reference position from the standard position by the magnification ratio.

In addition, in the positioning device according to the present disclosure, the processor may control the moving mechanism based on the movement amount to move the top plate, the radiation source, and the radiation detector relative to each other.

In addition, in the positioning device according to the present disclosure, the processor may display the movement amount.

In addition, in the positioning device according to the present disclosure, the processor may update the movement amount according to a relative movement of the top plate, the radiation source, and the radiation detector, and display the updated movement amount.

In addition, in the positioning device according to the present disclosure, the standard position in the positioning image may be a center of an irradiation field in the positioning image, the target structure may be a target bone, and the reference position in the target structure may be a centroid of the target bone.

The present disclosure relates to a radiation image processing device comprising at least one processor, in which the processor acquires a first radiation image and a second radiation image based on radiation having different energy distributions, which are acquired by imaging a subject in which a target bone is positioned by the positioning device according to the present disclosure, derives a bone part image obtained by extracting a bone part of the subject from the first radiation image and the second radiation image, and derives at least a bone mineral density of the target bone based on at least a pixel value of a region of the target bone in the bone part image.

Note that, in the radiation image processing device according to the present disclosure, the processor may remove a scattered ray component from the first radiation image and the second radiation image, and may perform derivation of the bone part image and derivation of the bone mineral density by using the first and the second radiation images from which the scattered ray component is removed.

The present disclosure relates to a positioning method of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the method comprising acquiring a positioning image acquired by imaging the subject by the radiography apparatus, specifying a standard position in the positioning image and a reference position in a target structure included in the subject in the positioning image, and deriving a relative movement amount of the top plate, the radiation source, and the radiation detector based on a deviation amount of the reference position from the standard position.

The present disclosure relates to a radiation image processing method comprising acquiring a first radiation image and a second radiation image based on radiation having different energy distributions, which are acquired by imaging a subject in which a target bone is positioned by the positioning device according to the present disclosure, deriving a bone part image obtained by extracting a bone part of the subject from the first radiation image and the second radiation image, and deriving at least a bone mineral density of the target bone based on at least a pixel value of a region of the target bone in the bone part image.

Note that the positioning method and the radiation image processing method according to the present disclosure may be provided as a radiation image processing program to be executed by a computer.

According to the present disclosure, reproducible positioning can be performed at the time of imaging the subject.

DETAILED DESCRIPTION

Figure 1:
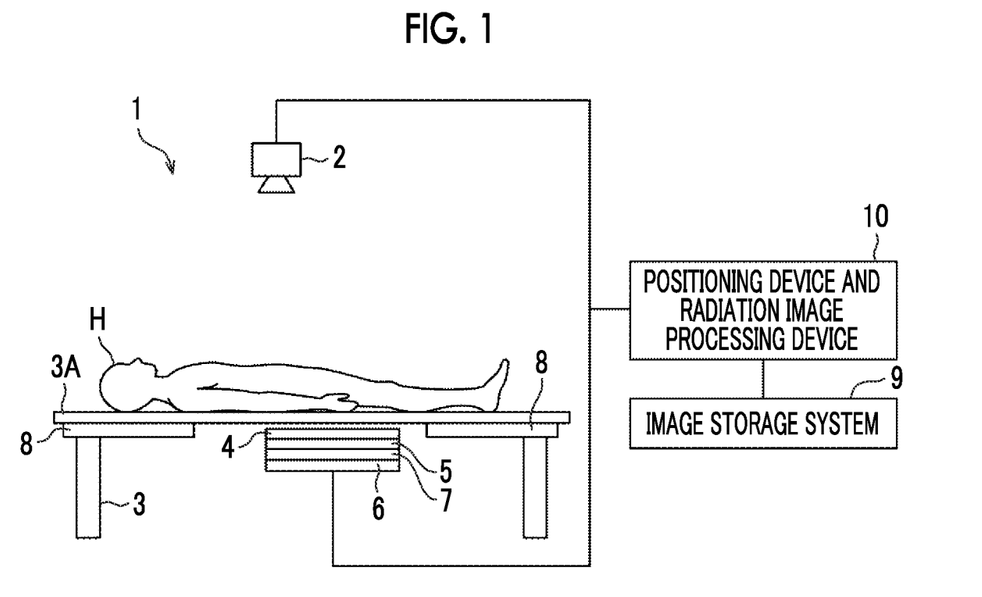
FIG. 1 is a schematic block diagram showing a configuration of a radiography system to which a positioning device and a radiation image processing device according to an embodiment of the present disclosure are applied.

In the following, an embodiment of the present disclosure will be described with reference to the drawings. FIG. 1 is a schematic block diagram showing a configuration of a radiography system to which a positioning device and a radiation image processing device according to the embodiment of the present disclosure are applied. As shown in FIG. 1, the radiography system according to the present embodiment comprises an imaging apparatus 1, a positioning device and radiation image processing device (hereinafter may be represented by the radiation image processing device) 10 according to the present embodiment.

The imaging apparatus 1 is an imaging apparatus that performs energy subtraction by a so-called one-shot method of converting radiation, such as X-rays, emitted from a radiation source 2 and transmitted through a subject H who lies on a top plate 3A of an imaging table 3 into energy and irradiating a first radiation detector 5 and a second radiation detector 6 with the converted radiation. At the time of imaging, as shown in FIG. 1, a scattered ray removal grid (hereinafter simply referred to as a grid) 4, the first radiation detector 5, a radiation energy conversion filter 7 made of a copper plate or the like, and the second radiation detector 6 are disposed in order from a side closest to the radiation source 2, and the radiation source 2 is driven. The first and second radiation detectors 5 and 6 are closely attached to the radiation energy conversion filter 7. Note that the grid 4, the first radiation detector 5, the radiation energy conversion filter 7, and the second radiation detector 6 are disposed below the top plate 3A of the imaging table 3 at a position facing the radiation source 2 across the top plate 3A.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. The first and second radiation images G1 and G2 are input to the radiation image processing device 10.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

Note that, in the imaging apparatus 1, in order to acquire a positioning image GP described below, the subject H may be imaged by using only one radiation detector. In this case, the first radiation detector 5 on a side closer to the radiation source 2 is used.

In addition, in the imaging apparatus 1, the radiation source 2, the first radiation detector 5, and the second radiation detector 6 are positioned such that an optical axis of the radiation emitted from the radiation source 2 is emitted to the center of the first radiation detector 5 and the second radiation detector 6. In addition, the imaging table 3 is positioned such that the top plate 3A is orthogonal to the optical axis of the radiation.

The grid 4 is configured by lead that does not transmit the radiation and an interspace material, such as aluminum or fiber that easily transmit the radiation which are disposed alternately with a fine grid density of about 4.0 lines/mm. By using the grid 4, a scattered ray component of the radiation transmitted through the subject H can be removed, but it cannot be completely removed. Therefore, the first and second radiation images G1 and G2 include a primary ray component of the radiation transmitted through the subject H as well as the scattered ray component.

Note that the primary ray component is a signal component having a pixel value represented by the radiation that reaches the radiation detector without being scattered by the subject H in the radiation that is transmitted through the subject H. On the other hand, the scattered ray component is a signal component having a pixel value represented by the radiation that reaches the radiation detector by being scattered by the subject H in the radiation that is transmitted through the subject H.

In addition, the imaging apparatus 1 comprises a moving mechanism 8 that two-dimensionally moves the top plate 3A in a direction intersecting the optical axis of the radiation emitted from the radiation source 2. Note that, in the present embodiment, the direction intersecting the optical axis of the radiation is a direction orthogonal to the optical axis (the right-left direction and the depth direction of the paper surface in FIG. 1, hereinafter referred to as a horizontal direction). The moving mechanism 8 can two-dimensionally move the top plate 3A in the horizontal direction, and can stop the top plate 3A at a predetermined stop position after the movement. Although not shown, as the moving mechanism 8, a known reciprocating unit or a known parallel movement unit, such as a belt movement unit that moves the top plate 3A by a motor and a belt connected to the motor, a movement unit by a motor and a drive screw and a traveling nut which are rotationally driven by the motor, and a movement unit by a motor and a gear, a pinion, and a rack which are rotationally driven by the motor, can be used. Note that the moving mechanism 8 may not comprise a motor and may manually move the top plate 3A.

In addition, the moving mechanism 8 is provided with a sensor (not shown) that measures the movement amount of the top plate 3A. As the sensor, a sensor that detects the movement amount on the paper surface in the right-left direction and the depth direction in FIG. 1 by detecting the rotation speed of the motor can be used. In addition, a sensor that measures the movement amount by providing a scale on the top plate 3A and counting the number of scales according to the movement of the top plate 3A may be used.

The radiation image processing device 10 is connected to an image storage system 9 via a network (not shown). The image storage system 9 is a system that stores image data of the radiation image captured by the imaging apparatus 1. The image storage system 9 extracts an image corresponding to a request from the radiation image processing device 10 from the stored radiation image and transmits the extracted image to a request source device. Specific examples of the image storage system 9 include picture archiving and communication systems (PACS).

Figure 2:
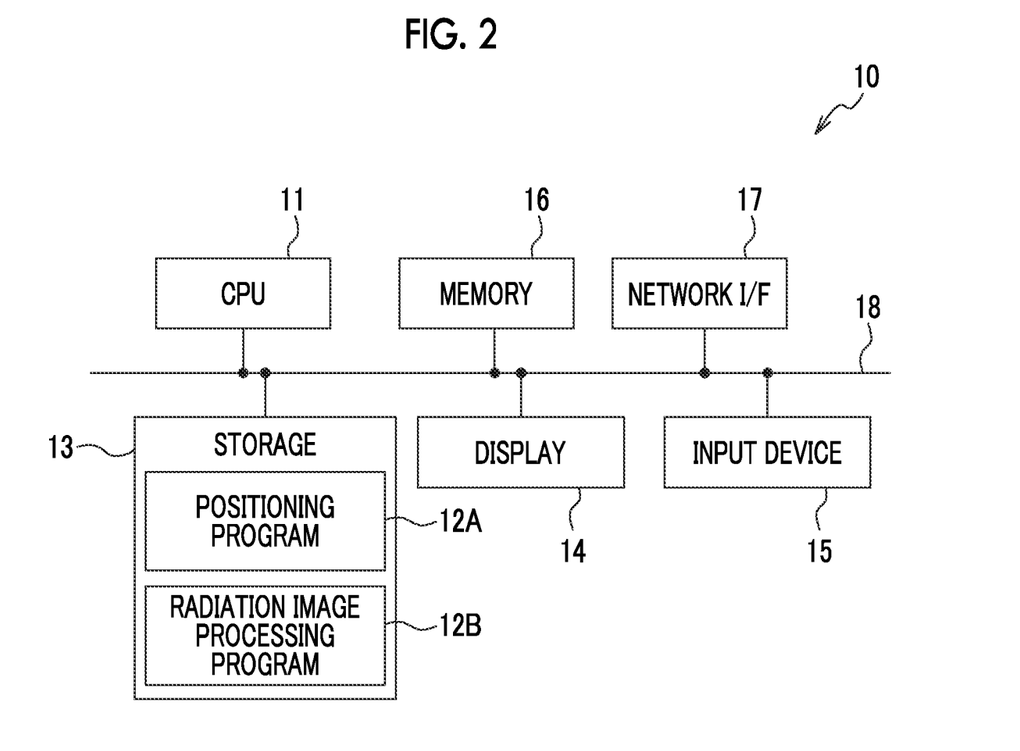
FIG. 2 is a diagram showing a schematic configuration of the positioning device and the radiation image processing device according to the present embodiment.

Then, the positioning device and the radiation image processing device according to the present embodiment will be described. First, with reference to FIG. 2, a hardware configuration of the positioning device and the radiation image processing device according to the present embodiment will be described. As shown in FIG. 2, the positioning device and radiation image processing device 10 is a computer, such as a workstation, a server computer, and a personal computer, and comprises a central processing unit (CPU) 11, a non-volatile storage 13, and a memory 16 as a transitory storage region. In addition, the positioning device and radiation image processing device 10 comprise a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores a positioning program 12A and a radiation image processing program 12B installed in the positioning device and radiation image processing device 10. The CPU 11 reads out the positioning program 12A and the radiation image processing program 12B from the storage 13 and expands the read out positioning program 12A and radiation image processing program 12B in the memory 16, and executes the expanded positioning program 12A and radiation image processing program 12B.

Note that the positioning program 12A and the radiation image processing program 12B are stored in a storage device of the server computer connected to the network or in a network storage in a state of being accessible from the outside, and are downloaded and installed in the computer that configures the positioning device and radiation image processing device 10 in response to the request. Alternatively, the positioning program 12A and the radiation image processing program 12B are distributed in a state of being recorded on a recording medium, such as a digital versatile disc (DVD) or a compact disc read only memory (CD-ROM), and are installed in the computer that configures the positioning device and radiation image processing device 10 from the recording medium.

Figure 3:
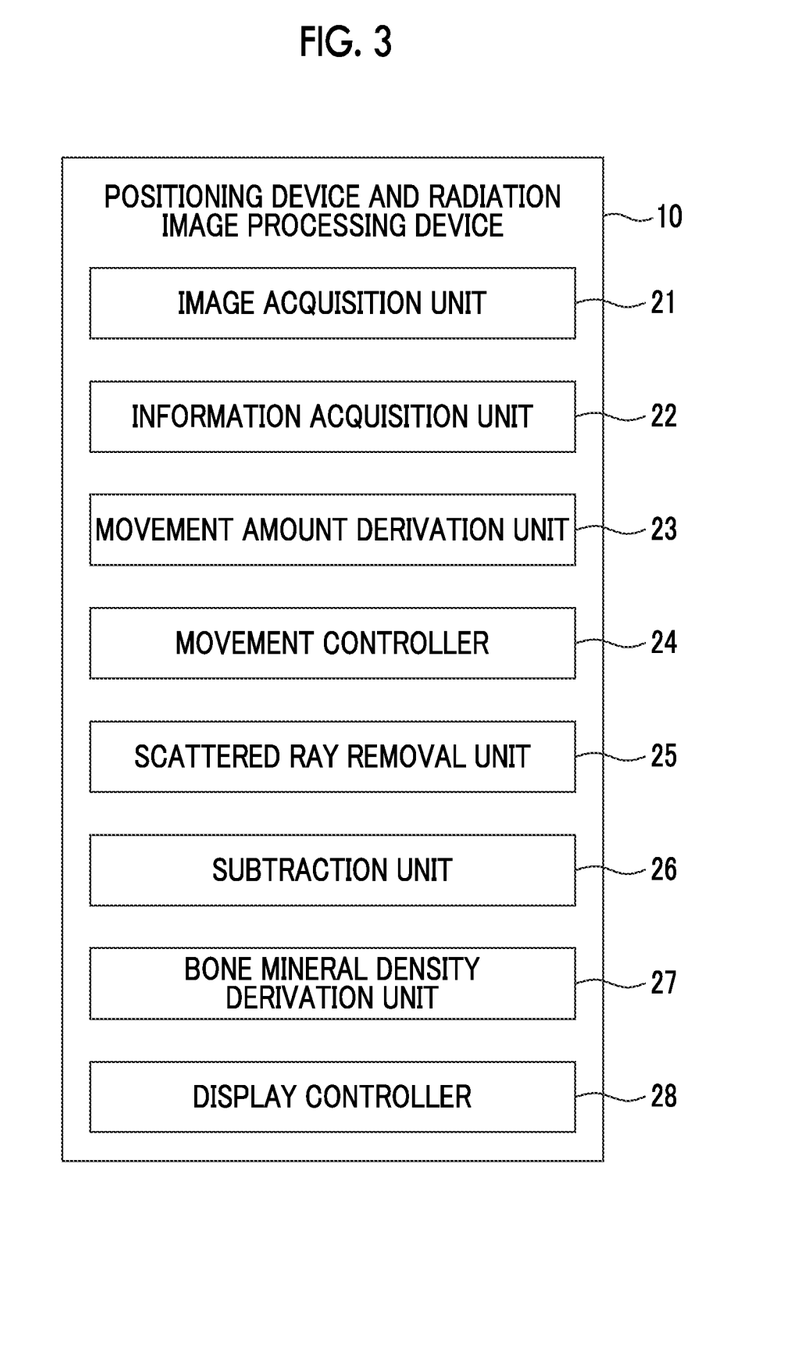
FIG. 3 is a diagram showing a functional configuration of the positioning device and the radiation image processing device according to the present embodiment.

Then, a functional configuration of the positioning device and the radiation image processing device according to the present embodiment will be described. FIG. 3 is a diagram showing the functional configuration of the positioning device and the radiation image processing device according to the present embodiment. As shown in FIG. 3, the positioning device and radiation image processing device 10 comprises an image acquisition unit 21, a position specifying unit 22, a movement amount derivation unit 23, a movement controller 24, a scattered ray removal unit 25, a subtraction unit 26, a bone mineral density derivation unit 27, and a display controller 28. Moreover, by executing the positioning program 12A, the CPU 11 functions as the image acquisition unit 21, the position specifying unit 22, the movement amount derivation unit 23, the movement controller 24, and the display controller 28. In addition, by executing the radiation image processing program 12B, the CPU 11 functions as the image acquisition unit 21, the scattered ray removal unit 25, the subtraction unit 26, the bone mineral density derivation unit 27, and the display controller 28.

In a case of performing positioning, the image acquisition unit 21 drives the radiation source 2 to irradiate the subject H with the radiation, detects the radiation transmitted through the subject H by the first radiation detector 5, and acquires the positioning image GP. The positioning image GP is used only for positioning the subject H and is not used for diagnosis. Therefore, in a case in which the positioning image GP is acquired, the radiation emitted to the subject H is set to a lower dose than in a case in which the radiation image used for diagnosis is acquired. Note that the positioning image GP may be acquired by the same dose of radiation as in a case in which the radiation image used for diagnosis is acquired. In a case in which the positioning image GP is acquired, the imaging condition, such as an imaging dose, a tube voltage, a source image receptor distance (SID) which is a distance between the radiation source 2 and the surface of the first radiation detector 5, and a source object distance (SOD) which is a distance between the radiation source 2 and a surface of the subject H, are set.

It is preferable that the SOD be acquired by, for example, a time of flight (TOF) camera. It is preferable that the SID be acquired by, for example, a potentiometer, an ultrasound range finder, a laser range finder, or the like. Another imaging condition need only be set by input from the input device 15 by a radiological technician who is an operator. The set imaging condition is stored in the storage 13.

In addition, in a case in which the bone mineral density is derived, the image acquisition unit 21 irradiates the subject H with the radiation by driving the radiation source 2, detects the radiation transmitted through the subject H by the first and second radiation detectors 5 and 6, and acquires the first and second radiation images G1 and G2. Also in this case, the imaging condition is set and stored in the storage 13.

Note that, in the present embodiment, the positioning image GP, the first radiation image G1, and the second radiation image G2 may be acquired by a program separate from the positioning program 12A and the radiation image processing program 12B and stored in the storage 13. In addition, in a case in which the positioning image GP, the first radiation image G1, and the second radiation image G2 are acquired in advance and stored in the image storage system 9, the image acquisition unit 21 may acquire these images from the image storage system 9. In this case, the image acquisition unit 21 reads out the positioning image GP, the first radiation image G1, and the second radiation image G2 stored in the storage 13 from the storage 13 for processing.

The position specifying unit 22 specifies a standard position P1 in the positioning image GP and a reference position P2 of the target structure included in the subject H in the positioning image GP. In the present embodiment, the standard position P1 in the positioning image GP is a center of an irradiation field in the positioning image GP. In a case in which the positioning image GP of the subject H is acquired without using the irradiation field stop, the center of the irradiation field is a centroid of the positioning image GP. In a case in which the positioning image GP is acquired using the irradiation field stop, the irradiation field center is a centroid of an irradiation field region in the positioning image GP.

In addition, in the present embodiment, the target structure is a fifth lumbar vertebra, and the reference position of the target structure is a centroid of the fifth lumbar vertebra. The fifth lumbar vertebra is an example of the target bone. Therefore, the position specifying unit 22 first specifies the fifth lumbar vertebra from the positioning image GP. The fifth lumbar vertebra need only be specified by using a trained neural network in which machine learning is performed to extract the fifth lumbar vertebra from the positioning image GP. In addition, a template representing the shape of the fifth lumbar vertebra may be stored in the storage 13, and the fifth lumbar vertebra may be specified by template matching between the template and the positioning image GP.

Figure 4:
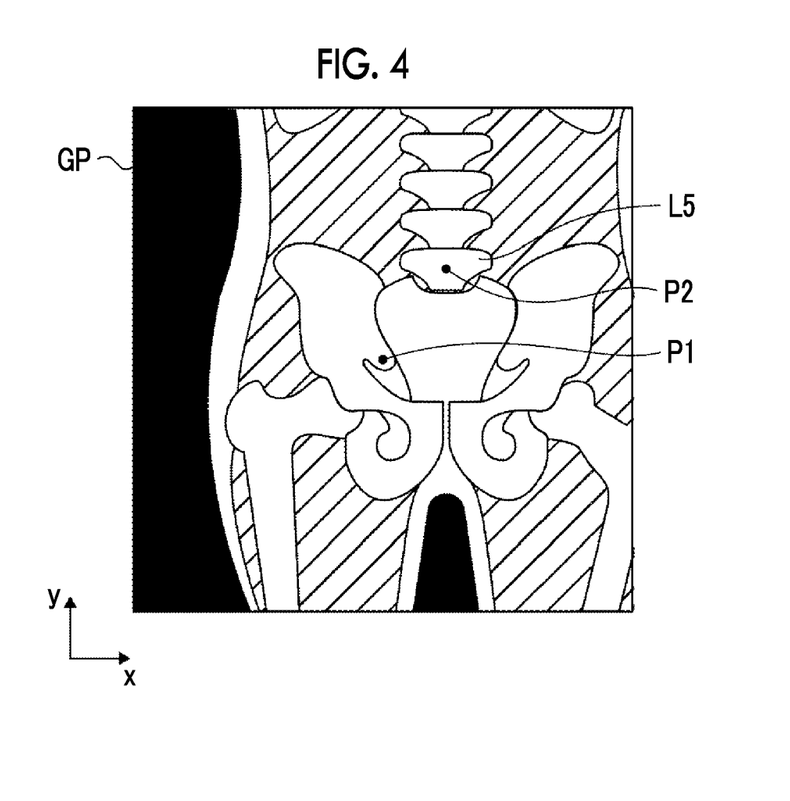
FIG. 4 is a diagram showing a positioning image.

Note that the fifth lumbar vertebra and the centroid of the fifth lumbar vertebra may be specified by displaying the positioning image GP on the display 14 and receiving an instruction for specifying the fifth lumbar vertebra and the centroid of the fifth lumbar vertebra by the operator using the input device 15. In this case, the position specifying unit 22 specifies the centroid of the specified fifth lumbar vertebra at the reference position P2. FIG. 4 is a diagram showing the positioning image GP. Note that FIG. 4 shows the specified standard position P1 and reference position P2. As shown in FIG. 4, it can be seen that the reference position P2 deviates from the standard position P1. Note that, in FIG. 4, the right-left direction is an x-direction, and the up-down direction is a y-direction. The x-direction and the y-direction correspond to the depth direction and the right-left direction in FIG. 1, respectively.

Figure 5:
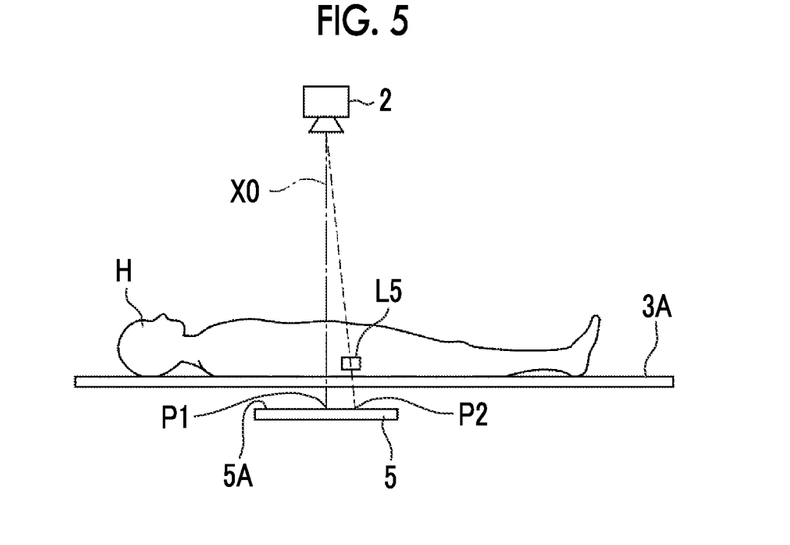
FIG. 5 is a diagram for describing a deviation between a reference position and a standard position.

The movement amount derivation unit 23 derives a relative movement amount of the top plate 3A, the radiation source 2, and the radiation detectors 5 and 6 based on a deviation amount of the reference position P2 from the standard position P1. FIG. 5 is a diagram for describing the deviation between the reference position P2 and the standard position P1. As shown in FIG. 5, in a case in which a fifth lumbar vertebra L5, which is the target bone of the subject H, is not positioned on an optical axis X0 of the radiation emitted from the radiation source 2, the position of the optical axis X0 and the position of the fifth lumbar vertebra L5 deviate from each other on a detection surface 5A of the radiation detector 5. As a result, in the positioning image GP, the reference position P2 deviates from the standard position P1 as shown in FIG. 4.

In the present embodiment, in order to allow the position of the optical axis X0 and the centroid of the fifth lumbar vertebra L5 to match each other, the movement amount derivation unit 23 first derives the deviation amount ($\Delta x0$, $\Delta y0$) between the standard position P1 and the reference position P2 on the positioning image GP. The deviation amount is a distance in the x-direction and a distance in the y-direction on the positioning image GP for allowing the reference position P2 and the standard position P1 to match each other.

On the other hand, since the target bone (fifth lumbar vertebra L5) is present in the subject H and the subject H is placed on the top plate 3A, the target bone is positioned at a position away from the detection surface 5A of the radiation detector 5. Therefore, the deviation amount between the centroid of the target bone and the optical axis X0 of the radiation in the subject H is magnified on the positioning image GP. As a result, even in a case in which the top plate 3A is moved by using the misregistration amount (Δx0,Δy0) derived on the positioning image GP as it is, the target bone and the optical axis X0 of the radiation cannot be allowed to match each other. In the present embodiment, the movement amount derivation unit 23 derives the movement amount of the top plate 3A in consideration of the fact that the deviation amount is magnified on the positioning image GP.

Figure 6:
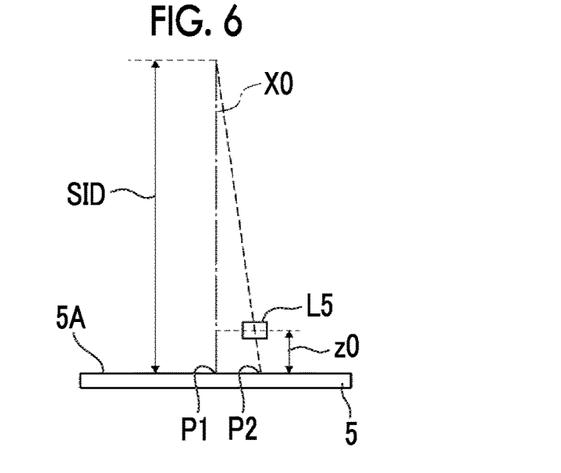
FIG. 6 is a diagram for describing the deviation between the reference position and the standard position.

Here, the positional relationship between the detection surface 5A of the radiation detector 5, the SID, and the fifth lumbar vertebra L5, which is the target bone, in a case in which the subject H is viewed from the side is as shown in FIG. 6. Therefore, the movement amount derivation unit 23 derives the movement amount (Δx1,Δy1) of the top plate 3A in the horizontal direction by Expression (1) by using the SID included in the imaging condition and the distance z0 between the centroid of the target bone and the detection surface 5A of the radiation detector 5.

$$\Delta x1 = \Delta x0 \times (SID-z0)/SID$$

$$\Delta y1 = \Delta y0 \times (SID-z0)/SID \quad (1)$$

The SID is included in the imaging condition. On the other hand, the distance of the target bone from the back side in the human body is anatomically substantially fixed according to the type of the target bone. For example, in a case in which the target bone is the fifth lumbar vertebra, the centroid of the fifth lumbar vertebra is at a distance about 3 cm from the back of the subject H, and in a case where the target bone is the femur, the centroid of the joint portion of the femur is at a distance about 10 cm from the back side of the subject H. Therefore, in the present embodiment, the average distance z0 of the centroid from the back of the human body is derived in advance according to the type of the target bone and stored in the storage 13. The movement amount derivation unit 23 reads out the distance z0 according to the type of the target bone from the storage 13 and uses the read out distance z0 for deriving the movement amount.

Note that the distance z0 may be prepared according to the gender, the age, the height, the weight, or the like of the subject H and stored in the storage 13, and the movement amount may be derived by using the distance z0 according to the gender, the age, the height, the weight, or the like of the subject H. In addition, in a case in which a three-dimensional image such as a CT image or an MRI image of the subject H to be imaged is stored in the image storage system 9, the distance of the centroid of the target bone from the back may be measured by using the three-dimensional image to derive the movement amount by using the measured value.

Figure 7:
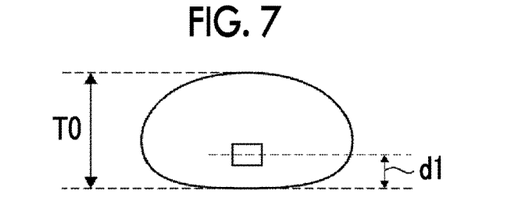
FIG. 7 is a diagram showing a relationship between a body thickness and a distance of a target bone from the back.

In addition, as shown in FIG. 7, a distance d1 of the target bone from the back is at a position at a substantially fixed ratio to the body thickness T0 of the subject H. For example, the distance d1 is at a position at a substantially fixed ratio, such as 0.3 in a case of the lumbar vertebra, or 0.5 in a case of the femur. Therefore, the movement amount derivation unit 23 may derive the distance d1 by deriving the body thickness T0 of the subject H by using the SID and the SOD included in the imaging condition and multiplying the derived body thickness T0 by a ratio R according to the target bone (T0×R). Here, the distance between the surface of the top plate 3A and the detection surface 5A of the radiation detector 5 is a value peculiar to the imaging apparatus 1. Therefore, in a case in which the distance between the surface of the top plate 3A and the detection surface 5A of the radiation detector 5 is defined as d2, the body thickness T0=SID−SOD−d2 is satisfied, and the distance z0 shown in FIG. 6 can be derived by z0=d1+d2. Note that the ratio R need only be stored in the storage 13 according to the type of the target bone.

The movement controller 24 controls the drive of the moving mechanism 8 based on the movement amount derived by the movement amount derivation unit 23, and moves the top plate 3A in the horizontal direction. That is, the movement controller 24 moves the top plate 3A by Δx1 in the x-direction and Δy1 in the y-direction. As a result, the optical axis X0 of the radiation emitted from the radiation source 2 and the centroid of the target bone of the subject H match each other. Note that the movement need only be started by a start instruction by the operator using the input device 15.

Figure 8:
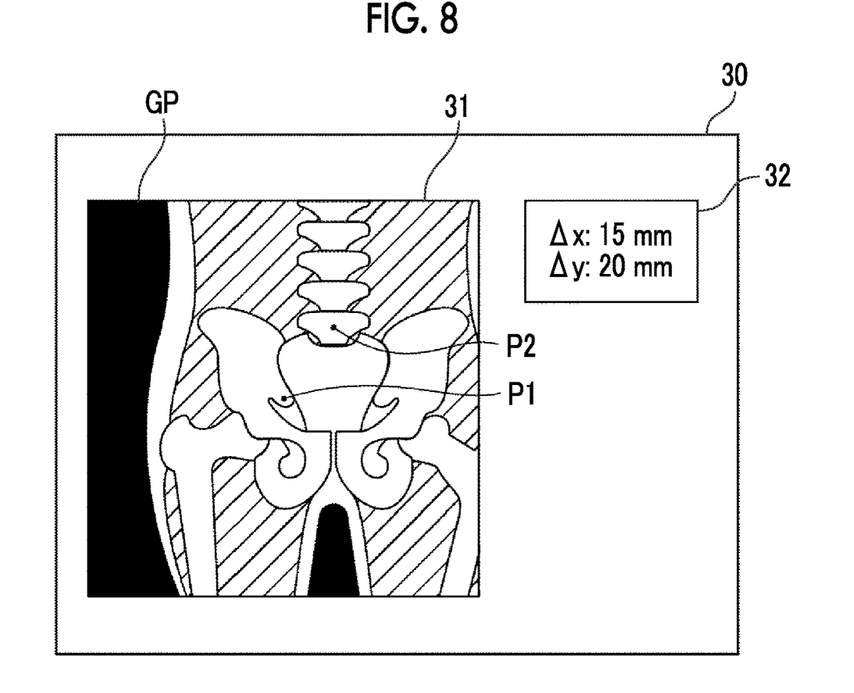
FIG. 8 is a diagram showing a display screen of a movement amount.

The display controller 28 displays the movement amount derived by the movement amount derivation unit 23 on the display 14. FIG. 8 is a diagram showing a display screen of the movement amount. As shown in FIG. 8, a display screen 30 includes an image display region 31 and a movement amount display region 32. The positioning image GP is displayed in the image display region 31. Note that, in FIG. 8, the standard position P1 and the reference position P2 in the positioning image GP are also displayed. In the movement amount display region 32, the movement amount derived by the movement amount derivation unit 23 is displayed. In the present embodiment, the output of the sensor of the moving mechanism 8 that detects the movement amount of the top plate 3A is input to the display controller 28. As a result, the movement amount displayed in the movement amount display region 32 is updated to be decreased as the top plate 3A is moved and the centroid of the target bone approaches the optical axis X0 of the radiation. Moreover, in a case in which the top plate 3A is moved by the derived movement amount, it is 0 in both the x-direction and the y-direction.

Figure 9:
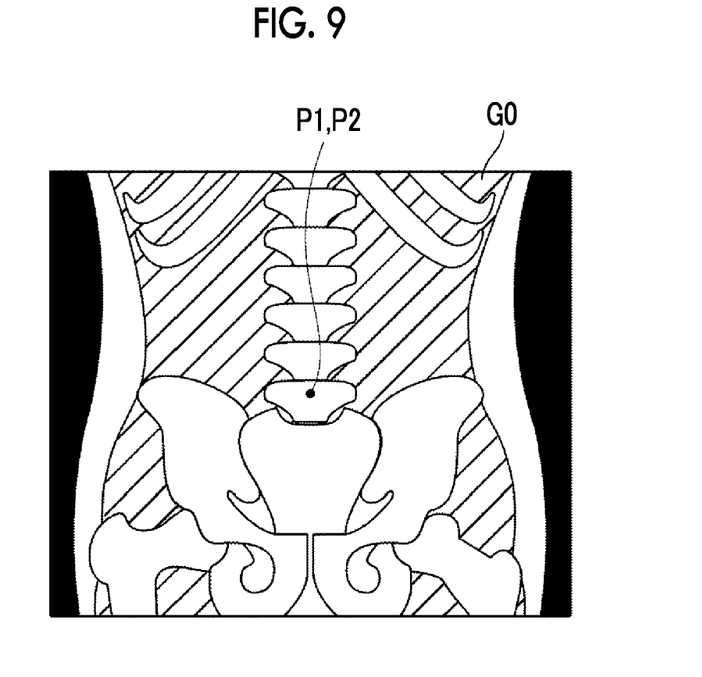
FIG. 9 is a diagram showing a radiation image acquired after positioning.

As a result, the positioning of the subject H is completed. In a case in which the subject H is imaged in a state in which the positioning is completed, the standard position P1 of the radiation image G0 and the reference position P2 which is the centroid of the fifth lumbar vertebra L5 match each other as shown in the radiation image G0 of FIG. 9, and the fifth lumbar vertebra L5 is positioned in the vicinity of the center of the radiation image G0.

In a case in which the positioning is completed as described above, the operator gives an instruction for imaging to derive the bone mineral density of the subject H by using the input device 15. As a result, the image acquisition unit 21 acquires the first radiation image G1 and the second radiation image G2 which are the front images of the subject H from the first and second radiation detectors 5 and 6 by causing the imaging apparatus 1 to image the subject H. In this case, the set imaging condition is stored in the storage 13.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 25 removes the scattered ray component from the first radiation image G1 and the second radiation image G2. For example, the scattered ray removal unit 25 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

In the following, the removal of the scattered ray component from the first radiation image G1 will be described, but the removal of the scattered ray component from the second radiation image G2 can also be performed in the same manner. First, the scattered ray removal unit 25 acquires a virtual model K of the subject H having an initial body thickness distribution $T0(x,y)$. The virtual model K is data virtually representing the subject H of which a body thickness depending on the initial body thickness distribution $T0(x,y)$ is associated with a coordinate position of each pixel of the first radiation image G1. Note that the virtual model K of the subject H having the initial body thickness distribution $T0(x,y)$ may be stored in the storage 13 in advance. In addition, a body thickness distribution $T(x,y)$ of the subject H may be calculated based on the SID and the SOD included in the imaging condition. In this case, the body thickness distribution can be obtained by subtracting, from the SID, the distance between the surface of the SOD and the top plate 3A and the detection surface 5A of the radiation detector 5.

Next, the scattered ray removal unit 25 generates, based on the virtual model K, an image obtained by combining an estimated primary ray image in which a primary ray image obtained by imaging the virtual model K is estimated and an estimated scattered ray image in which a scattered ray image obtained by imaging the virtual model K is estimated as an estimated image in which the first radiation image G1 obtained by imaging the subject H is estimated.

Next, the scattered ray removal unit 25 corrects the initial body thickness distribution $T0(x,y)$ of the virtual model K such that a difference between the estimated image and the first radiation image G1 is small. The scattered ray removal unit 25 repeatedly performs the generation of the estimated image and the correction of the body thickness distribution until the difference between the estimated image and the first radiation image G1 satisfies a predetermined termination condition. The scattered ray removal unit 25 derives the body thickness distribution in a case in which the termination condition is satisfied as the body thickness distribution $T(x,y)$ of the subject H. In addition, the scattered ray removal unit 25 removes the scattered ray component included in the first radiation image G1 by subtracting the scattered ray component in a case in which the termination condition is satisfied from the first radiation image G1. On the other hand, the scattered ray removal unit 25 also performs the scattered ray removal processing on the second radiation image G2 in the same manner as in the first radiation image G1.

Figure 10:
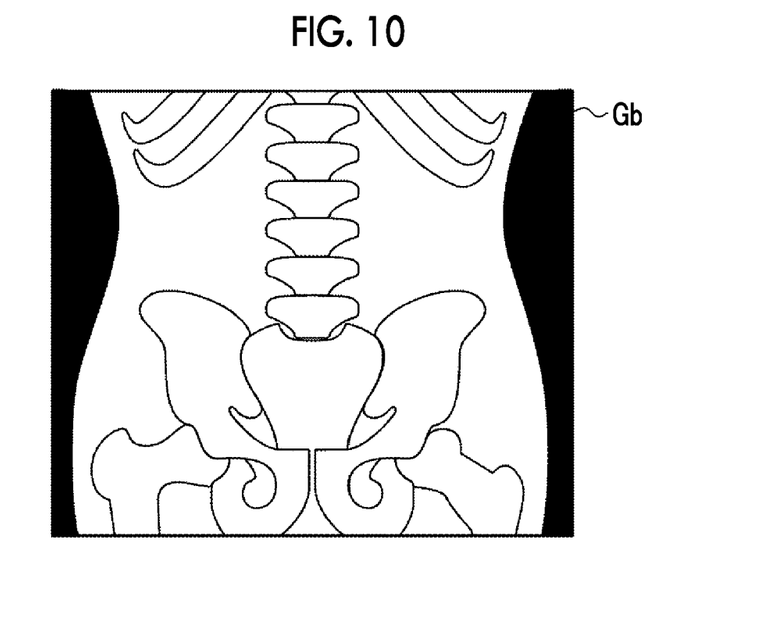
FIG. 10 is a diagram showing a bone part image.

The subtraction unit 26 derives a bone part image Gb obtained by extracting the bone part of the subject H from the first and second radiation images G1 and G2, which have been subjected to the scattered ray removal processing, by performing the energy subtraction processing. Note that, in the first and second radiation images G1 and G2 in the subsequent processing, the scattered ray component is removed. In a case in which the bone part image Gb is derived, the subtraction unit 26 performs weighting subtraction between the corresponding pixels with respect to the first and second radiation images G1 and G2 as shown in Expression (2) to generate the bone part image Gb in which the bone part of the subject H included in each of the radiation images G1 and G2 is extracted, as shown in FIG. 10. In Expression (2), a is a weighting coefficient. Note that a pixel value of each pixel in a bone region in the bone part image Gb is a bone part pixel value.

$$Gb(x,y)=\alpha \cdot G2(x,y)-G1(x,y) \quad (2)$$

In the present embodiment, since the positioning is performed as described above, the centroid of the fifth lumbar vertebra L5, which is the target bone, and the optical axis X0 of the radiation match each other. Therefore, as shown in FIG. 10, the fifth lumbar vertebra L5 in the bone part image Gb is positioned in the vicinity of the center of the bone part image Gb.

The bone mineral density derivation unit 27 derives the bone mineral density for each pixel of the bone part image Gb. In the present embodiment, the bone mineral density derivation unit 27 derives a bone mineral density B by converting each pixel value of the bone part image Gb into the pixel value of the bone part image acquired under a standard imaging condition. Specifically, the bone mineral density derivation unit 27 derives the bone mineral density by correcting each pixel value of the bone part image Gb by using a correction coefficient acquired from a look-up table described below.

Here, the contrast between the soft part and the bone part in the radiation image is lower as the tube voltage in the radiation source 2 is higher and the energy of the radiation emitted from the radiation source 2 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 11:
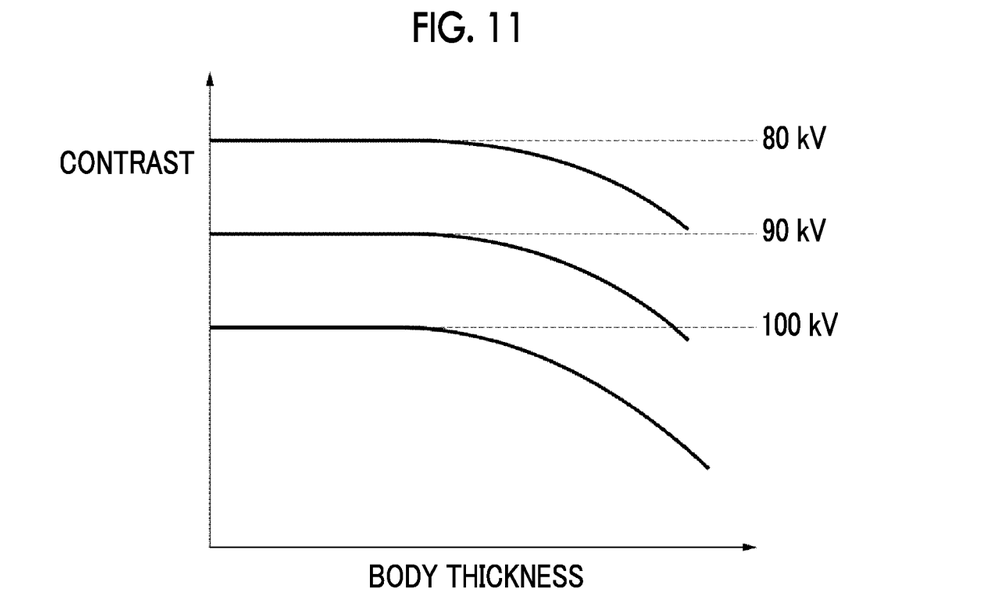
FIG. 11 is a diagram showing a relationship of a contrast between a bone part and a soft part with respect to a body thickness of a subject.

FIG. 11 is a diagram showing a relationship of the contrast between the bone part and the soft part with respect to the body thickness of the subject H. Note that FIG. 11 shows the relationship of the contrast between the bone part and the soft part with respect to the body thickness of the subject H at the three tube voltages of 80 kV, 90 kV, and 100 kV. As shown in FIG. 11, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 11 shifts to a higher contrast side as the pixel value of the bone region in the bone part image Gb is increased.

In the present embodiment, the look-up table for acquiring the correction coefficient for correcting the difference in the contrast depending on the tube voltage at the time of imaging and the reduction in the contrast due to the influence of the beam hardening in the bone part image Gb is stored in the storage 13 of the radiation image processing device 10. The correction coefficient is the coefficient for correcting each pixel value of the bone part image Gb.

Figure 12:
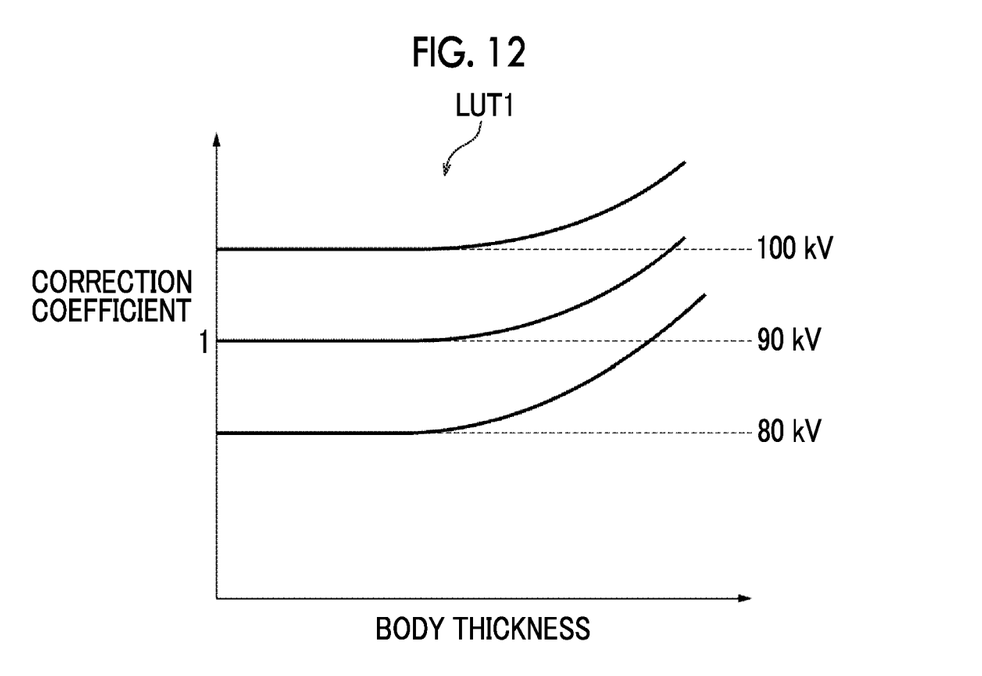
FIG. 12 is a diagram showing an example of a look-up table.

FIG. 12 is a diagram showing an example of the look-up table for acquiring the correction coefficient. In FIG. 12, a look-up table (hereinafter simply referred to as a table) LUT1 in which the standard imaging condition is set to the tube voltage of 90 kV is shown. As shown in FIG. 12, in the table LUT1, the correction coefficient is set to be larger as the tube voltage is higher and the body thickness of the subject H is larger. In the example shown in FIG. 11, since the standard imaging condition is the tube voltage of 90 kV, the correction coefficient is 1 in a case in which the tube voltage is 90 kV and the body thickness is 0. Note that although the table LUT1 is shown in two dimensions in FIG. 12, the correction coefficient differs depending on the pixel value of the bone region. Therefore, the table LUT1 is actually a three-dimensional table to which an axis representing the pixel value of the bone region is added.

The bone mineral density derivation unit 27 extracts the body thickness distribution T(x,y) of the subject H and a correction coefficient $C0(x,y)$ for each pixel depending on the imaging condition including a set value of the tube voltage stored in the storage 13 from the table LUT1. Moreover, as shown in Expression (3), the bone mineral density derivation unit 27 multiplies each pixel (x,y) of the bone region in the bone part image Gb by the correction coefficient $C0(x,y)$ to derive a bone mineral density B(x,y) (g/cm$^2$) for each pixel of the bone part image Gb. The bone mineral density B(x,y) derived in this way is acquired by imaging the subject H by the tube voltage of 90 kV, which is the standard imaging condition, and shows the pixel value of the bone region included in the radiation image from which the influence of the beam hardening is removed.

$$B(x,y)=C0(x,y) \times Gb(x,y) \tag{3}$$

Figure 13:
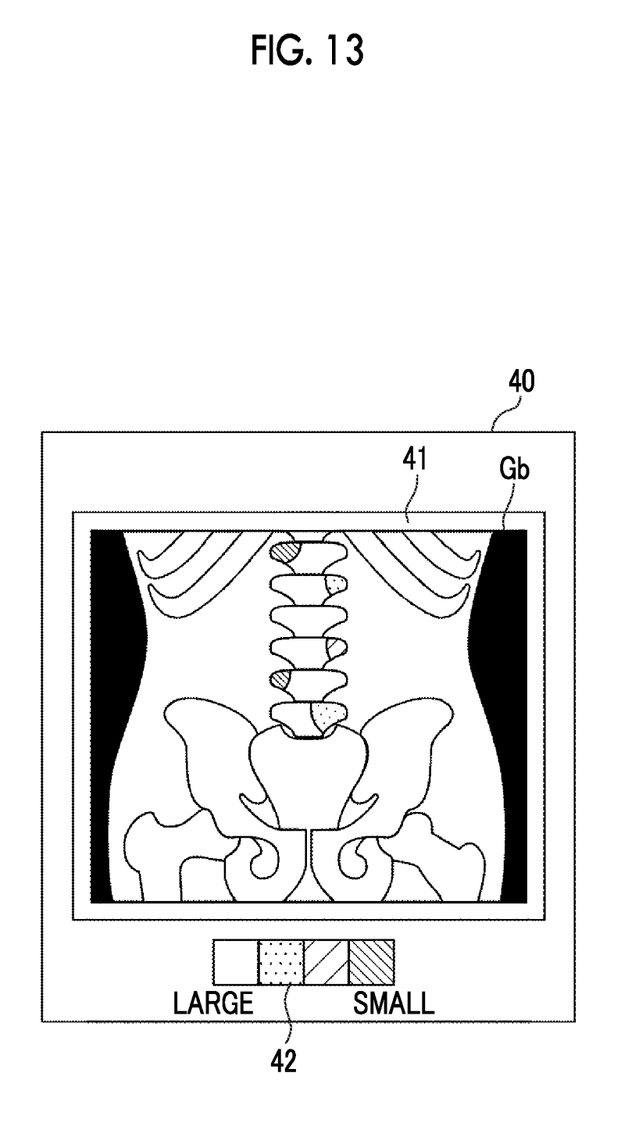
FIG. 13 is a diagram showing a display screen of a bone mineral density.

The display controller 28 displays the bone mineral density derived by the bone mineral density derivation unit 27 on the display 14. FIG. 13 is a diagram showing a display screen of the bone mineral density. As shown in FIG. 13, the display screen 40 has a bone mineral density display region 41.

The bone part image Gb is displayed in the bone mineral density display region 41. In the bone part image Gb, a pattern is added to the bone region depending on the bone mineral density. Note that, in FIG. 13, for the sake of simplicity, the pattern representing the bone mineral density is added only to the vertebra including the fifth lumbar vertebra L5. Below the bone mineral density display region 41, a reference 42 representing the magnitude of the bone mineral density for the added pattern is displayed. An operator can easily recognize the bone mineral density by interpreting the bone part image Gb while referring to the reference 42. Note that different colors may be added to the bone part image Gb depending on the bone mineral density instead of the pattern.

Note that the fifth lumbar vertebra L5 and other vertebrae in the bone part image Gb need only be specified by using the trained neural network that is trained through machine learning to extract the fifth lumbar vertebra L5 and the like from the bone part image Gb. In addition, templates representing the fifth lumbar vertebra L5 and the like may be stored in the storage 13, and specifying may be performed by performing template matching between the templates and the bone part image Gb.

Figure 14:
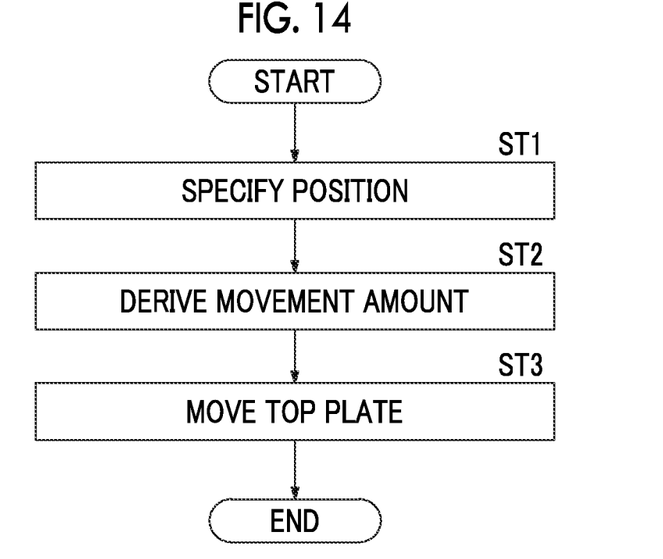
FIG. 14 is a flowchart of positioning processing performed in the present embodiment.

Then, processing performed in the present embodiment will be described. FIG. 14 is a flowchart showing positioning processing performed in the present embodiment. Note that the positioning image GP is acquired by the image acquisition unit 21 and stored in the storage 13. In a case in which a processing start instruction is given, the position specifying unit 22 specifies the standard position P1 in the positioning image GP and the reference position P2 of the target structure included in the subject H in the positioning image GP (position specifying: step ST1).

Further, the movement amount derivation unit 23 derives a relative movement amount of the top plate 3A, the radiation source 2, and the radiation detectors 5 and 6 based on a deviation amount of the reference position P2 from the standard position P1 (step ST2). Moreover, the movement controller 24 controls the drive of the moving mechanism 8 based on the movement amount derived by the movement amount derivation unit 23, and moves the top plate 3A in the horizontal direction (step ST3), and terminates the positioning processing.

Figure 15:
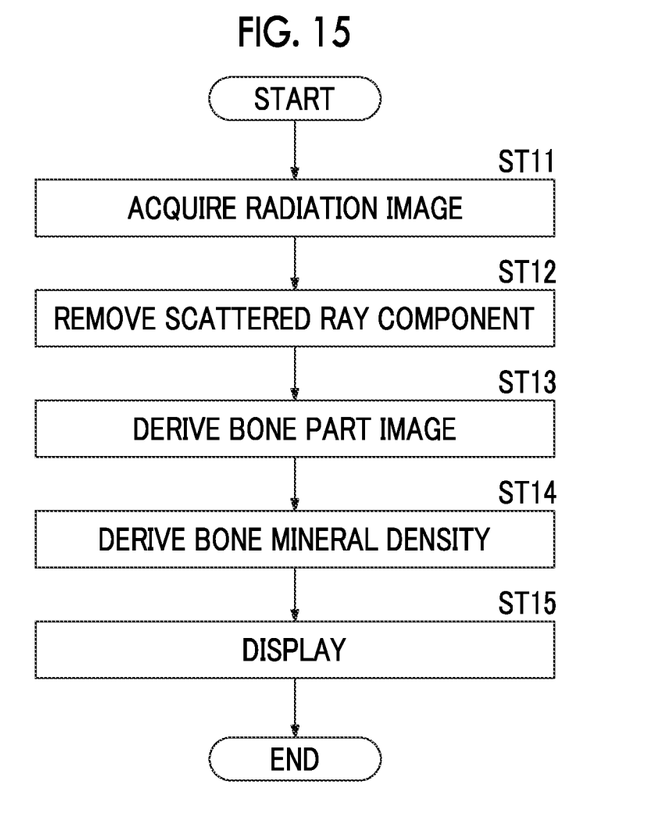
FIG. 15 is a flowchart of radiation image processing performed in the present embodiment.

Then, radiation image processing according to the present embodiment will be described. FIG. 15 is a flowchart showing the radiation image processing performed in the present embodiment. After the positioning is performed as described above, the processing is started by the instruction for imaging, and the image acquisition unit 21 performs the energy subtraction imaging of the subject H to acquire the first and second radiation images G1 and G2 (radiation image acquisition; step ST11). Then, the scattered ray removal unit 25 removes the scattered ray component from the first and second radiation images G1 and G2 (step ST12). Subsequently, the subtraction unit 26 derives the bone part image Gb in which the bone part of the subject H is extracted from the first and second radiation images G1 and G2 (step ST13).

Subsequently, the bone mineral density derivation unit 27 derives the bone mineral density for each pixel of the bone part image Gb (step ST14). Further, the display controller 28 displays the bone mineral density on the display 14 (step ST15), and terminates the processing.

As described above, in the present embodiment, the standard position P1 in the positioning image GP and the reference position P2 in the target bone included in the subject H in the positioning image GP are specified, and the relative movement amount of the top plate 3A, the radiation source 2, and the radiation detector 5 is derived based on the deviation amount of the reference position P2 from the standard position P1. Therefore, by moving the top plate 3A, the radiation source 2, and the radiation detector 5 relative to each other based on the derived movement amount, the target bone can be allowed to match the optical axis X0 of the radiation. Therefore, the radiological technician who is the operator can position the subject H such that the target bone is positioned at a desired position without repeating trial and error. Therefore, regardless of the skill of the radiological technician who is the operator, reproducible positioning can be easily performed at the time of imaging the subject H.

In addition, it is possible to allow the reference position P2 of the target structure and the optical axis X0 of the radiation to match each other with higher accuracy by deriving the magnification ratio of the target structure on the positioning image, correcting the deviation amount of the reference position P2 from the standard position P1 by the magnification ratio, and deriving the movement amount.

In addition, in the present embodiment, after the subject H is positioned, the first and second radiation images G1 and G2 are acquired by performing the energy subtraction imaging, the bone part image Gb is derived from the first and second radiation images G1 and G2, and the bone mineral density is derived based on the bone part image Gb. Therefore, the bone part image Gb can be acquired in a state in which the target bone is always positioned at the center position. Therefore, it is possible to derive the bone mineral density in which the error due to the different positioning of the target bone is reduced, especially in a case in which the follow-up is performed. Therefore, the follow-up of the bone mineral density can be performed with higher accuracy.

Note that, in the embodiment described above, the movement controller 24 controls the drive of the moving mechanism 8 based on the movement amount derived by the movement amount derivation unit 23, and moves the top plate 3A in the horizontal direction, but the present disclosure is not limited to this. By receiving the operation by the operator using the input device 15, the moving mechanism 8 may be controlled to move the top plate 3A in the horizontal direction. For example, in a case in which the input device 15 is a keyboard, the moving mechanism 8 may be operated by the instruction using the arrow keys in the up-down and right-left directions to move the top plate 3A in the horizontal direction. In this case, the movement amount displayed on the display 14 is updated according to the movement of the top plate 3A, and in a case in which the top plate 3A is moved by the derived movement amount, it is 0 in both the x-direction and the y-direction. Therefore, the operator need only move the top plate 3A until the movement amount is 0 while observing the displayed movement amount.

In addition, the radiological technician who is the operator may move the top plate 3A horizontally without providing the moving mechanism 8. Even in this case, it is possible for the operator to easily position the subject H by displaying the movement amount on the display 14.

In addition, in the embodiment described above, the movement amount derivation unit 23 derives the movement amount of the top plate 3A in consideration of the fact that the deviation amount is magnified on the positioning image GP, but the present disclosure is not limited to this. The deviation amount ($\Delta x0, \Delta y0$) between the standard position P1 and the reference position P2 on the positioning image GP may be derived as the movement amount without considering that the deviation amount is magnified. In this case, even in a case in which the top plate 3A is moved in the horizontal direction based on the derived movement amount, the centroid of the target bone and the optical axis X0 of the radiation may not exactly match. However, in a case of a relatively large bone such as the lumbar vertebra, the optical axis X0 of the radiation is present in the target bone even in a case in which the centroid of the target bone and the optical axis X0 of the radiation do not exactly match. Therefore, it is possible to substantially allow the target bone and the optical axis X0 of the radiation to match each other.

In addition, in the embodiment described above, the centroid of the target bone and the optical axis X0 of the radiation are allowed to match each other by moving the top plate 3A in the horizontal direction, the present disclosure is not limited to this. The centroid of the target bone and the optical axis X0 of the radiation may be allowed to match each other by providing another moving mechanism that integrally moves the radiation source 2 and the radiation detectors 5 and 6 in parallel to the top plate 3A in the imaging apparatus 1 instead of the moving mechanism 8, and integrally moving the radiation source 2 and the radiation detectors 5 and 6 in parallel to the top plate 3A by using the other moving mechanism. Note that, in addition to the moving mechanism 8, another moving mechanism may be provided. In this case, since the top plate 3A, the radiation source 2, and the radiation detectors 5 and 6 can be moved at the same time, the centroid of the target bone and the optical axis X0 of the radiation can be quickly allowed to match each other.

In addition, in the embodiment described above, the fifth lumbar vertebra L5 of the subject H is used as the target bone, but the present disclosure is not limited to this. Any bone other than the fifth lumbar vertebra L5, such as the vertebra, the femur, and the calcaneus, can be used as the target bone according to the purpose of diagnosis. In addition, the target structure allowed to match the optical axis X0 of the radiation is not limited to the bone. Organs such as lungs, liver, and heart according to the purpose of diagnosis may be used as the target structure.

In addition, in the embodiment described above, the positioning processing and the radiation image processing are performed by using the radiation image acquired by the system that images the first and second radiation images G1 and G2 of the subject H by using the first and second radiation detectors 5 and 6, it is needless to say that the present embodiment can be applied to even in the system that acquires the radiation image of the subject by using an accumulative phosphor sheet instead of the radiation detector. In this case, the positioning image GP need only be acquired by irradiating one accumulative phosphor sheets with the radiation transmitted through the subject H, accumulating and recording radiation image information of the subject H in the accumulative phosphor sheets, and photoelectrically reading the radiation image information from the accumulative phosphor sheets. The first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet. In this case, the accumulative phosphor sheet is an example of the radiation detector.

In addition, the radiation in the embodiment described above is not particularly limited, and $\alpha$-rays or $\gamma$-rays can be used in addition to X-rays.

In addition, in the embodiment described above, various processors shown below can be used as the hardware structures of processing units that execute various pieces of processing, such as the image acquisition unit 21, the position specifying unit 22, the movement amount derivation unit 23, the movement controller 24, the scattered ray removal unit 25, the subtraction unit 26, the bone mineral density derivation unit 27, and the display controller 28. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. A positioning device of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the positioning device comprising:
at least one processor,
wherein the processor
acquires a positioning image acquired by imaging the subject by the radiography apparatus,
specifies a standard position in the positioning image and a reference position in a target structure included in the subject in the positioning image,
derives a magnification ratio of the target structure on the positioning image based on an imaging distance in a case in which the positioning image is acquired, and a distance between the radiation detector and the target structure, and
derives a relative movement amount of the top plate, the radiation source, and the radiation detector by correcting a deviation amount of the reference position from the standard position by the magnification ratio.

2. The positioning device according to claim 1,
wherein the processor
specifies the target structure in the positioning image, and
specifies the reference position by deriving the reference position in the specified target structure.

3. The positioning device according to claim 1,
wherein the processor
displays the positioning image, and
specifies the reference position by receiving designation of the reference position in the displayed positioning image.

4. The positioning device according to claim 1,
wherein the processor controls the moving mechanism based on the movement amount to move the top plate, the radiation source, and the radiation detector relative to each other.

5. The positioning device according to claim 1,
wherein the processor displays the movement amount.

6. The positioning device according to claim 5,
wherein the processor
updates the movement amount according to a relative movement of the top plate, the radiation source, and the radiation detector, and
displays the updated movement amount.

7. The positioning device according to claim 1,
wherein the standard position in the positioning image is a center of an irradiation field in the positioning image,
the target structure is a target bone, and
the reference position in the target structure is a centroid of the target bone.

8. A radiation image processing device comprising:
at least one processor,
wherein the processor
acquires a first radiation image and a second radiation image based on radiation having different energy distributions, which are acquired by imaging a subject in which a target bone is positioned by the positioning device according to claim 1,
derives a bone part image obtained by extracting a bone part of the subject from the first radiation image and the second radiation image, and
derives at least a bone mineral density of the target bone based on at least a pixel value of a region of the target bone in the bone part image.

9. The radiation image processing device according to claim 8,
wherein the processor
removes a scattered ray component from the first radiation image and the second radiation image, and
performs derivation of the bone part image and derivation of the bone mineral density by using the first and the second radiation images from which the scattered ray component is removed.

10. A radiation image processing method comprising:
acquiring a first radiation image and a second radiation image based on radiation having different energy distributions, which are acquired by imaging a subject in which a target bone is positioned by the positioning device according to claim 1;
deriving a bone part image obtained by extracting a bone part of the subject from the first radiation image and the second radiation image; and
deriving at least a bone mineral density of the target bone based on at least a pixel value of a region of the target bone in the bone part image.

11. A positioning method of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the method comprising:
acquiring a positioning image acquired by imaging the subject by the radiography apparatus;
specifying a standard position in the positioning image and a reference position in a target structure included in the subject in the positioning image;
deriving a magnification ratio of the target structure on the positioning image based on an imaging distance in a case in which the positioning image is acquired, and a distance between the radiation detector and the target structure;

deriving a relative movement amount of the top plate, the radiation source, and the radiation detector by correcting a deviation amount of the reference position from the standard position by the magnification ratio.

12. A positioning device of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the positioning device comprising:
at least one processor,
wherein the processor
acquires a positioning image acquired by imaging the subject by the radiography apparatus,
specifies a standard position in the positioning image and a reference position in a target structure included in the subject in the positioning image,
derives a magnification ratio of the target structure on the positioning image based on an imaging distance in a case in which the positioning image is acquired, a body thickness of the subject, and a ratio of a position at which the target structure is present to the body thickness, and
derives a relative movement amount of the top plate, the radiation source, and the radiation detector by correcting a deviation amount of the reference position from the standard position by the magnification ratio.

13. The positioning device according to claim 12, wherein the processor
specifies the target structure in the positioning image, and
specifies the reference position by deriving the reference position in the specified target structure.

14. The positioning device according to claim 12, wherein the processor
displays the positioning image, and
specifies the reference position by receiving designation of the reference position in the displayed positioning image.

15. The positioning device according to claim 12, wherein the processor controls the moving mechanism based on the movement amount to move the top plate, the radiation source, and the radiation detector relative to each other.

16. The positioning device according to claim 12, wherein the processor displays the movement amount.

17. The positioning device according to claim 16 wherein the processor
updates the movement amount according to a relative movement of the top plate, the radiation source, and the radiation detector, and
displays the updated movement amount.

18. The positioning device according to claim 12, wherein the standard position in the positioning image is a center of an irradiation field in the positioning image, the target structure is a target bone, and
the reference position in the target structure is a centroid of the target bone.

19. A radiation image processing device comprising:
at least one processor,
wherein the processor
acquires a first radiation image and a second radiation image based on radiation having different energy distributions, which are acquired by imaging a subject in which a target bone is positioned by the positioning device according to claim 12,
derives a bone part image obtained by extracting a bone part of the subject from the first radiation image and the second radiation image, and
derives at least a bone mineral density of the target bone based on at least a pixel value of a region of the target bone in the bone part image.

20. The radiation image processing device according to claim 19,
wherein the processor
removes a scattered ray component from the first radiation image and the second radiation image, and
performs derivation of the bone part image and derivation of the bone mineral density by using the first and the second radiation images from which the scattered ray component is removed.

21. A radiation image processing method comprising:
acquiring a first radiation image and a second radiation image based on radiation having different energy distributions, which are acquired by imaging a subject in which a target bone is positioned by the positioning device according to claim 12;
deriving a bone part image obtained by extracting a bone part of the subject from the first radiation image and the second radiation image; and
deriving at least a bone mineral density of the target bone based on at least a pixel value of a region of the target bone in the bone part image.

22. A positioning method of a subject in a radiography apparatus including a radiation source that irradiates the subject with radiation, a top plate on which the subject is placed, at least one radiation detector that is disposed at a position facing the radiation source across the top plate, and derives a radiation image of the subject by detecting the radiation transmitted through the subject, and a moving mechanism that moves the top plate, the radiation source, and the radiation detector relative to each other in a direction intersecting an optical axis of the radiation, the method comprising:
acquiring a positioning image acquired by imaging the subject by the radiography apparatus;
specifying a standard position in the positioning image and a reference position in a target structure included in the subject in the positioning image;
deriving a magnification ratio of the target structure on the positioning image based on an imaging distance in a case in which the positioning image is acquired, a body thickness of the subject, and a ratio of a position at which the target structure is present to the body thickness; and
deriving a relative movement amount of the top plate, the radiation source, and the radiation detector by correcting a deviation amount of the reference position from the standard position by the magnification ratio.

* * * * *